United States Patent
Lee et al.

(10) Patent No.: US 11,204,423 B2
(45) Date of Patent: Dec. 21, 2021

(54) MICRO ROBOT AND MICRO ROBOT BEHAVIOR MEASUREMENT SYSTEM

(71) Applicant: DAEGU GYEONGBUK INSTITUTE OF SCIENCE AND TECHNOLOGY, Daegu (KR)

(72) Inventors: Hyun Ki Lee, Daegu (KR); Jin Young Kim, Gyeonggi-do (KR); Sung Jun Lim, Gyeonggi-do (KR); Hong Soo Choi, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 103 days.

(21) Appl. No.: 16/557,165

(22) Filed: Aug. 30, 2019

(65) Prior Publication Data
US 2020/0072980 A1 Mar. 5, 2020

(30) Foreign Application Priority Data
Sep. 4, 2018 (KR) .......... 10-2018-0105318

(51) Int. Cl.
*G01S 17/66* (2006.01)
*G01S 17/06* (2006.01)

(52) U.S. Cl.
CPC ........... *G01S 17/66* (2013.01); *G01S 17/06* (2013.01)

(58) Field of Classification Search
CPC ... G01S 17/66; G01S 17/06; A61B 2090/376; A61B 2034/303; A61B 2034/731; A61B 34/72; A61B 2017/00411; A61B 2017/00345; A61B 2017/00876; A61B 34/30; A61B 2034/2055; A61K 49/0091; A61K 49/0067; A61K 41/00; B25J 7/00; B25J 9/1005; B25J 19/02; A61M 31/00
See application file for complete search history.

(56) References Cited

U.S. PATENT DOCUMENTS

| | | | | |
|---|---|---|---|---|
| 2011/0270434 | A1* | 11/2011 | Fischer | B82Y 5/00 700/117 |
| 2012/0153226 | A1* | 6/2012 | Comanzo | C09K 11/7792 252/301.6 F |
| 2012/0228386 | A1* | 9/2012 | Wu | G01N 33/54386 235/488 |
| 2015/0297086 | A1* | 10/2015 | Hong | G01N 21/6456 600/431 |
| 2017/0084776 | A1* | 3/2017 | Gessner | H01L 31/125 |
| 2017/0143830 | A1* | 5/2017 | Wang | A61K 9/0009 |
| 2019/0015930 | A1* | 1/2019 | Berg | H01S 3/005 |

FOREIGN PATENT DOCUMENTS

| JP | 2001-179700 A | 7/2001 |
|---|---|---|
| KR | 20130045001 A | 5/2013 |

OTHER PUBLICATIONS

Wang, Ben et al., "Recent progress on micro- and nano-robots: towards in vivo tracking and localization", *Quant Imaging Med Surg*, 2018, vol. 8, No. 5, pp. 461-479.
Korean Office Action for Patent Application No. KR 10-2018-0105318 dated Dec. 13, 2019; 6 pages.

* cited by examiner

*Primary Examiner* — Thanh Luu
*Assistant Examiner* — Monica T Taba
(74) *Attorney, Agent, or Firm* — Harness, Dickey & Pierce, P.L.C.

(57) ABSTRACT

A micro robot that is moveable in a body includes first quantum dots.

11 Claims, 5 Drawing Sheets

MICRO ROBOT AND MICRO ROBOT BEHAVIOR MEASUREMENT SYSTEM

CROSS-REFERENCE TO RELATED APPLICATION

This application claims priority to Korean Patent Applications No. 10-2018-0105318, filed on Sep. 4, 2018 in the Korean Intellectual Property Office, the entirety of which is hereby incorporated by reference herein.

BACKGROUND

1. Field

The present disclosure relates to a micro robot, and more particularly, to a micro robot, a behavior of which may be measured by using quantum dots, and a system for measuring behavior of a micro robot.

2. Description of Related Art

A micro robot is a structure that delivers drugs, cells, etc. to a desired location in a body part such as a micro-vessel, cerebrospinal fluid, an eyeball, etc. Such a micro robot is driven by various methods that use a chemical reaction with surrounding fluid, acoustic energy or magnetic energy from outside, or biological propulsion such as mobility of bacteria.

As a micro robot technology using one of the above driving methods, a technology of forming a polymer structure by using a three-dimensional (3D) lithography technique, coating the polymer structure with a magnetic body and a biocompatible material, and shipping, growing, and delivering drugs or cells in the body by being controlled by an external magnetic field has been suggested.

In addition, methods of measuring behavior of a micro robot by using X-ray or fluorescent substance after the micro robot is inserted into the body have been suggested. However, when the X-ray is used, there is a concern about that a patient is exposed to a high-energy radiation and there may be a hardware interference with a system for driving the micro robot. When the fluorescent substance is used, it may be difficult to measure the behavior by using a small amount of fluorescent substance and it is difficult to perform real-time measurement due to a large size of the measurement system. Also, it is impossible to measure rotation of the micro robot by using the above methods.

SUMMARY

The present disclosure provides a micro robot and a system for measuring behavior of a micro robot, wherein behavior of a micro robot may be measured stably without a risk of exposure to high-energy radiation.

However, the above technical feature is exemplary and the scope of the disclosure is not limited thereto.

Additional aspects are set forth in part in the description which follows and, in part, may be apparent from the description, or may be learned by practice of the presented embodiments of the disclosure.

According to an embodiment of the disclosure, a micro robot that is moveable in a body, the micro robot includes first quantum dots.

The micro robot may further include a body portion comprising a magnetic portion, the body portion being moved by an external electromagnetic field, wherein the first quantum dots are arranged on the body portion.

The body portion may be coated with the first quantum dots.

The first quantum dots may absorb irradiated light of a near infrared ray wavelength band or a shortwave infrared ray (SWIR) band, and emit light of the SWIR band.

The micro robot may further include second quantum dots arranged on different locations from locations of the first quantum dots, the second quantum dots absorbing light emitted from the first quantum dots.

The body portion may include a first area and a second area that are symmetrically arranged based on a first axis that is in parallel with a moving direction of the micro robot, the first quantum dots may be on the first area, and the second quantum dots may be on the second area.

The micro robot may further include a body portion including a magnetic portion, the body portion being moved by an external electromagnetic field; and an indicator located at an end or an intermediate portion of the body portion, the indicator having the quantum dots arranged thereon.

The micro robot may further include a body portion comprising a magnetic portion, the body portion being moved by an external electromagnetic field, wherein the first quantum dots are arranged inside the body portion.

The body portion may be embedded with the first quantum dots.

According to an embodiment of the disclosure, a system for measuring a behavior of a micro robot, the system includes: a light source for irradiating light; the micro robot comprising first quantum dots that absorb light irradiated from the light source and emit light; and a detection unit sensing the light emitted from the first quantum dots.

The light source may irradiate light of a near infrared ray band or a shortwave infrared ray (SWIR) band, and the first quantum dots may absorb the irradiated light of the near infrared ray wavelength band or the SWIR wavelength band and emit light of the SWIR wavelength band.

The micro robot may include a body portion including a magnetic portion, the body portion being moved by an external electromagnetic field, the first quantum dots may be arranged on the body portion.

The micro robot may further include second quantum dots arranged on different locations from locations of the first quantum dots, the second quantum dots absorbing light emitted from the first quantum dots.

The body portion may include a first area and a second area that are symmetrically arranged based on a first axis that is in parallel with a moving direction of the micro robot, the first quantum dots may be on the first area, the second quantum dots may be on the second area, and the detection unit may detect rotation of the micro robot by using a difference in intensity of the detected light.

Other aspects, features and advantages of the disclosure will become better understood through the accompanying drawings, the claims and the detailed description.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
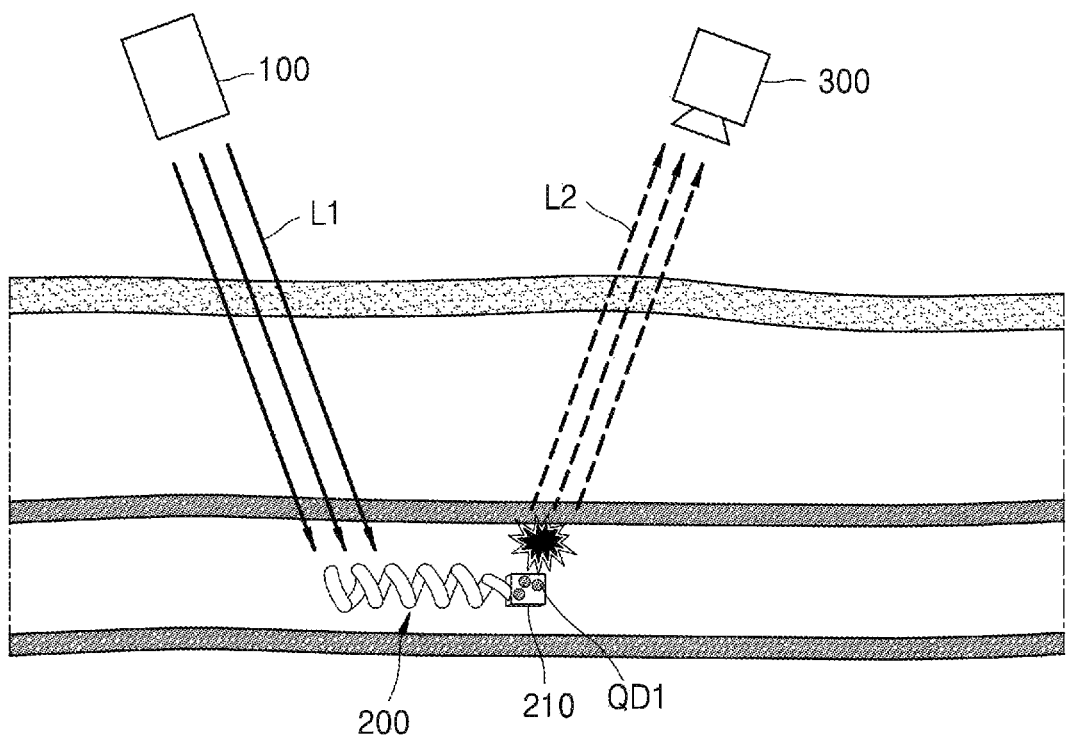
FIG. 1 is a conceptual diagram illustrating a system for measuring behavior of a micro robot, according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

In the present disclosure, the expression "include" or "may include" refers to existence of a corresponding function, operation, or element, and does not limit one or more additional functions, operations, or elements. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

In the present disclosure, the expression "or" includes any or all combinations of words enumerated together. For example, the expression "A or B" may include A, may include B, or may include both A and B.

In the present disclosure, expressions including ordinal numbers, such as "first" and "second," etc., may modify various elements. However, such elements are not limited by the above expressions. For example, the above expressions do not limit the sequence and/or importance of the elements. The above expressions are used merely for the purpose of distinguishing an element from the other elements. For example, a first user device and a second user device indicate different user devices although both of them are user devices. For example, a first element could be termed a second element, and similarly, a second element could be also termed a first element without departing from the scope of the present disclosure.

In the case where an element is referred to as being "connected" or "accessed" to other elements, it should be understood that not only the element is directly connected or accessed to the other elements, but also another element may exist between them. Contrarily, when an element is referred to as being "directly coupled" or "directly connected" to any other element, it should be understood that no element is interposed therebetween.

The terms used in the present disclosure are only used to describe specific embodiments, and are not intended to limit the present disclosure. An expression used in the singular encompasses the expression of the plural, unless it has a clearly different meaning in the context.

Unless defined otherwise, all terms used herein, including technical and scientific terms, have the same meaning as commonly understood by those of skill in the art to which the present disclosure pertains.

Such terms as those defined in a generally used dictionary are to be interpreted to have the meanings equal to the contextual meanings in the relevant field of art, and are not to be interpreted to have ideal or excessively formal meanings unless clearly defined in the present disclosure.

Figure 2:
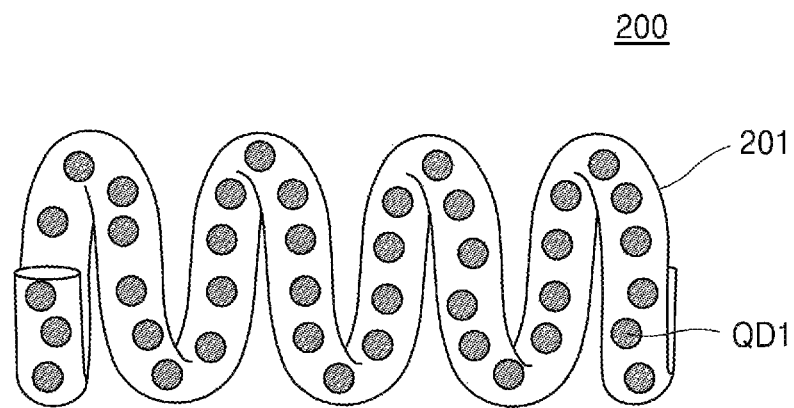
FIG. 2 is a diagram of a micro robot of FIG. 1.
Figure 3:
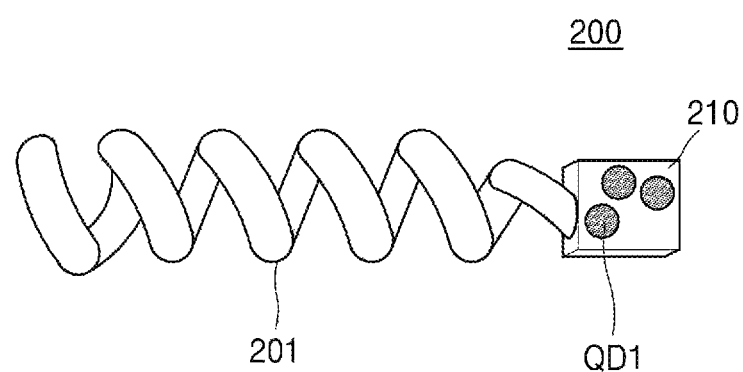
FIG. 3 is a diagram of a micro robot of FIG. 1.

FIG. 1 is a conceptual diagram of a measurement system 10 for measuring behavior of a micro robot, according to an embodiment, and FIGS. 2 and 3 are diagrams of a micro robot 200 of FIG. 1.

According to the related art, as an imaging technique for measuring behavior of a micro robot that moves in a body, magnetic resonance imaging (MRI), computed tomography (CT) or X-ray imaging, ultrasound wave, an optical coherence tomography (OCT) or confocal microscope may be used.

However, the above techniques may exhibit coherence with a system for driving a micro robot or difficulty in real-time measurement of an in-body micro robot. In detail, the MRI is a technique of measuring a signal generated when hydrogen nucleus of the body resonates by using a magnetic field, and it is impossible to use surgical instruments in or around MRI equipment due to a strong magnetic field, and thereby it is difficult to implement a real-time tracking system. When the CT or X-ray imaging is used, unnecessary X-ray exposure occurs in order to measure the behavior, and it is difficult to perform a continuous imaging operation for a long period of time due to a possibility of biological and gene destruction. Also, when the ultrasound wave is used, a velocity variation and distortion according to a medium may occur, and it is difficult to perform the measurement exactly due to a low resolution and S/N ratio. In addition, when the OCT or confocal microscope is used, a measurement depth is only about maximum 2 mm, the measurement may not be performed when there is water, and noise caused by various auto-fluorescence may occur.

According to the micro robot and the system for measuring behavior of the micro robot of the embodiment, the behavior of an in-body micro robot is measured by using quantum dots.

Referring to FIG. 1 to FIG. 3, the measurement system 10 for measuring behavior of a micro robot according to an embodiment may include a light source 100, the micro robot 200, and a detection unit 300.

The light source 100 may include all kinds of source devices that may generate light, for example, a light-emitting diode that may emit light of a certain wavelength band, or laser. The light source 100 is on outside a body, and may irradiate light towards the micro robot 200 that is inserted into the body and moved in the body. Here, since the light has to be irradiated to the micro robot 200 in the body, light of a wavelength band having a high in-vivo permeability has to be irradiated. Therefore, the light source 100 may emit light of a wavelength within a near-infrared ray band (that is, about 750 nm to about 1 µm) in an electromagnetic spectrum or light of a wavelength within a short wave infrared ray (SWIR) band (that is, about 2 µm to about 2.5 µm)

The micro robot 200 may have first quantum dots. The micro robot 200 may have any type of structure provided that the structure is moveable in the body, and may be driven by various methods, e.g., methods of using chemical reactions with surrounding fluid, acoustic energy or magnetic energy from outside, biological propulsion such as mobility of bacteria, etc. However, in the specification herein, a case in which the micro robot 200 is driven by using magnetic energy will be described for convenience of description.

The micro robot 200 may include a body portion 201 having a magnetic portion and being moved by an external electromagnetic field. For example, the micro robot 200 may have a polymer-based structure coated with a magnetic material and having a size of 101 to 102 μm. The magnetic portion may be in the body portion 201 or on the body portion 201 by coating the body portion 201 entirely or partially with a thin film including a magnetic material. The magnetic portion may include a magnetic material that is metal having magnetism of a certain strength and low corrosiveness, for example, may include iron oxide (—$Fe_2O_3$, $Fe_{2O4}$) or at least one selected from the group consisting of nickel (Ni), iron oxide (—$Fe_2O_3$, $Fe_{2O4}$), cobalt (Co), and neodymium (Nd).

In addition, the micro robot 200 may function as a human body simulation chip (human-on-a chip or body-on-a-chip) because the micro robot 200 is driven to be moveable in the body. The micro robot 200 reproduces human organs in miniature form on a small microfluidic chip by using microfluidic technology and cell culturing technology, and is a technique that precisely predicts physiological reactions of chemicals, medicines, etc. in the body and further is evaluated as a replacement for animal testing. The micro robot 200 may have a screw shape or a windmill shape as shown in the drawings, in order to properly implement a dynamic environment such as a variation in velocities of different fluids in the human body system.

An external surface of the micro robot 200 may be coated with a protective layer including a biocompatible material. Such a biocompatible material may include, for example, single or mixed form of titanium (Ti), medical stainless steel, alumina, or gold (Ag). The micro robot 200 is driven by an external magnetic field applied from the magnetic portion and a magnetic field coil system disposed on outside the body, and a rotation speed or a rotating direction of the micro robot 200 is changed according to a size or direction of the external magnetic field to control a velocity or a direction of the fluid in a biological network.

In addition, the micro robot 200 according to the embodiment may include first quantum dots QD1. Here, each of the first quantum dots QD1 absorbs light irradiated from outside and irradiates light of a certain wavelength band, for example, the first quantum dot QD1 may absorb the irradiated light of near infrared ray band or SWIR band and emit the light of the SWIR band. As described above, since the measuring system 10 of the behavior of the micro robot measures the behavior of the micro robot 200 in the body by using light, the measurement system 10 may use the wavelength band having high in-vivo permeability. Therefore, the first quantum dots QD1 included in the micro robot 200 may be quantum dots emitting infrared ray having high in-vivo permeability.

In addition, each of the first quantum dots QD1 may include a colloidal semiconductor nano-particle obtained through a chemical reaction in a solution. The first quantum dot QD1 may have a core-shell structure, in which a core may be formed of a material selected from a group I-IV compound such as AgS, $AgS_3$, etc., a group III-V compound such as InAs, etc., a group II-VI compound such as HgS, HgSe, $Hg_xCd_{1-x}S$, $Hg_xCd_{1-x}Se$, etc., and a group IV-VI compound such as PbS, PbSe, etc. The first quantum dot QD1 may have a shell including a material such as ZnS, etc. having greater bandgap energy and higher chemical stability than those of the core on a surface of the core having the above particle composition, so as to have high emission efficiency and stability.

In an embodiment, as shown in FIG. 2, the micro robot 200 may have the first quantum dots QD1 on the body portion 201. Here, the first quantum dots QD1 may be at least partially coated on a surface of the body portion 201. In other words, the first quantum dots QD1 may be coated at least partially on the body portion 201 of the micro robot 200 through a coating process, after fabricating the micro robot 200. However, one or more embodiments of the disclosure are not limited thereto, and in another embodiment, the first quantum dots QD1 may be included in a material of the body portion 201 so as to be included in the body portion 201, when the body portion 201 of the micro robot 200 is manufactured.

In another embodiment, as shown in FIG. 3, the micro robot 200 may further include an indicator 210 at an end of the body portion 201, and the first quantum dots QD1 may be at the indicator 210. The indicator 210 may be coated with the first quantum dots QD1 or may include the first quantum dots QD1 therein. The indicator 210 may be fabricated simultaneously with the body portion 201, but may be fabricated through a separate process and coupled to the end of the body portion 201.

Referring back to FIG. 1, the detection unit 300 may sense the light that is re-emitted from the first quantum dots QD1. The detection unit 300 may be arranged on outside the body like the light source 100, and senses the light emitted from the micro robot 200 in the body. The detection unit 300 may include an SWIR camera that may sense the light of the SWIR band emitted from the first quantum dots QD1.

As described above, the measurement system 10 for the behavior of the micro robot according to the embodiment may measure the behavior of the micro robot 200 in real-time safely without hardware interference with the system driving the micro robot 200 or a risk of radiation exposure, by irradiating light of the near infrared ray band or SWIR band to the micro robot 200 including the quantum dots and sensing the light emitted from the micro robot 200. In particular, the measurement system 10 according to the embodiment may precisely measure the behavior of the micro robot 200 because the quantum dots emitting the light of the SWIR band having high in-vivo permeability are used.

Figure 4:
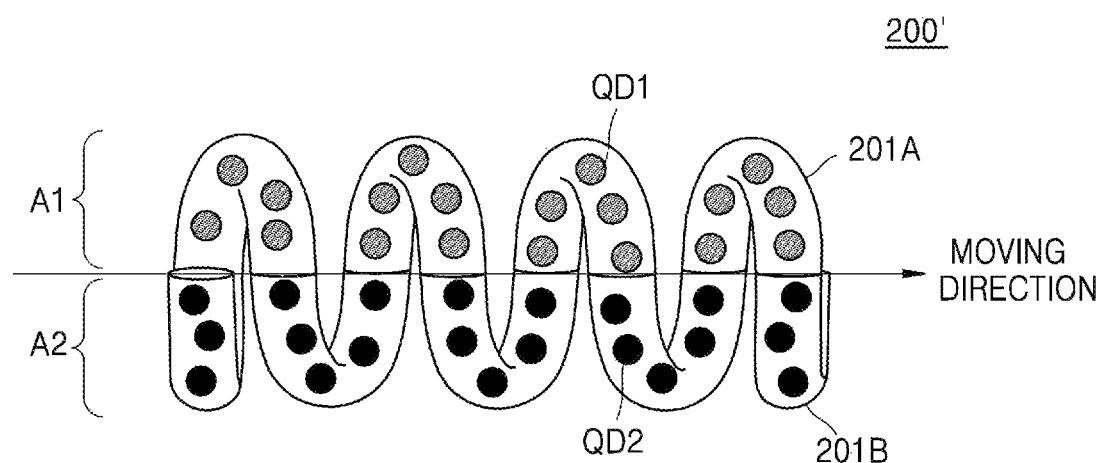
FIG. 4 is a diagram of a micro robot according to another embodiment.
Figure 5:
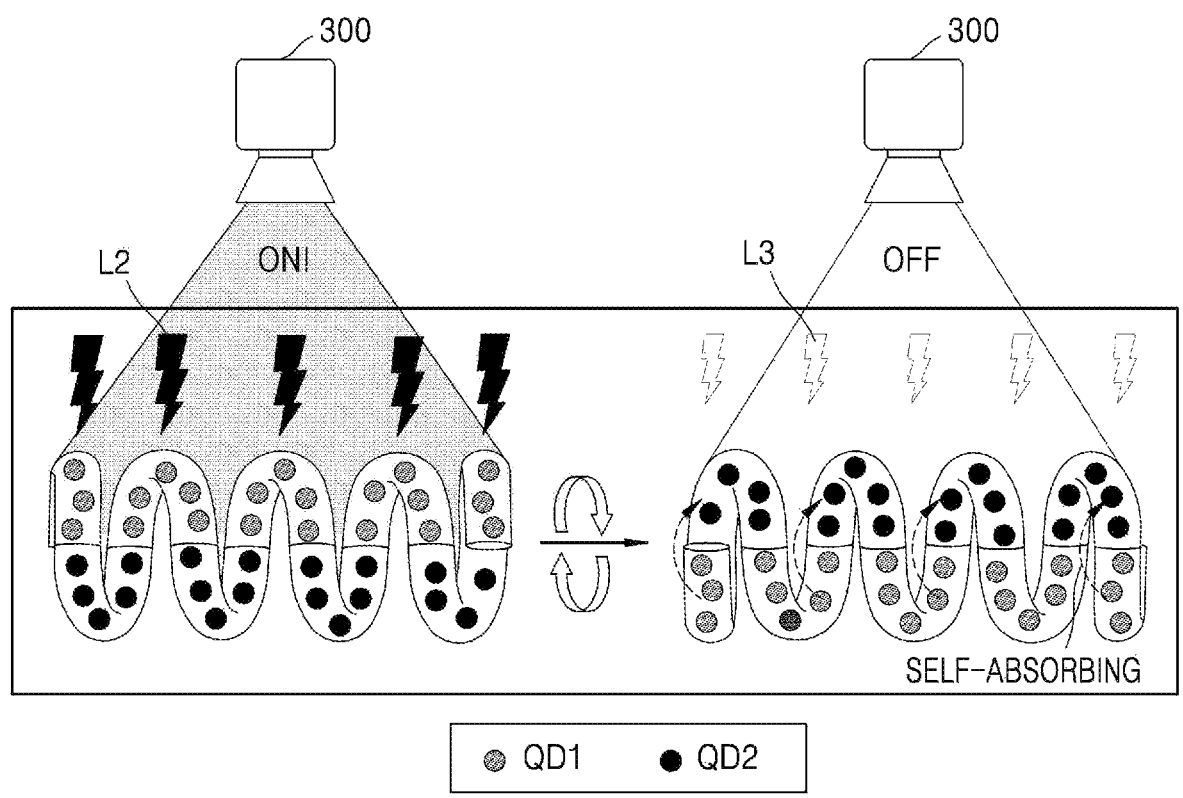
FIG. 5 is a diagram illustrating principles of measuring a rotation behavior of the micro robot of FIG. 4.

FIG. 4 is a diagram of a micro robot 200' according to another embodiment, and FIG. 5 is a diagram illustrating principles of measuring a rotating behavior of the micro robot 200' of FIG. 4.

Referring to FIGS. 4 and 5, the micro robot 200' according to the embodiment may include the first quantum dots QD1 and second quantum dots QD2 that is on a different location from that of the first quantum dots QD1 and absorbs the light emitted from the first quantum dots QD1. In detail, as shown in FIG. 4, the body portion 201 of the micro robot 200' may include a first area A1 and a second area A2 that are symmetrically arranged based on a first axis that is in parallel with a moving direction. Here, the first quantum dots QD1 may be on a first body portion 201A corresponding to the first area A1 and the second quantum dots QD2 may be on a second body portion 201B corresponding to the second area A2.

The micro robot 200' may have a pinwheel shape or a spiral shape for implementing the dynamic environment such as changed in velocities of different fluids in the human body system, and thereby moving in the fluid while rotating. Therefore, when the micro robot 200' moves while rotating, the locations of the first body portion 201A and the second body portion 201B may be switched repeatedly.

Here, since different kinds of quantum dots are arranged on the first body portion 201A and the second body portion 201B in the micro robot 200' according to the embodiment, the intensity of light emitted from the micro robot 200' may be changed, and then, the rotating behavior of the micro robot 200' may be measured by sensing the changed light intensity.

In detail, the first quantum dots QD1 may emit the light of SWIR band as described above. Here, the second quantum dots QD2 may function as a quencher absorbing the light emitted from the first quantum dots QD1. Referring to FIG. 5, when the light is irradiated by the light source 100 towards the micro robot 200', the first quantum dots QD1 on the first body portion 201A absorb the irradiated light and then emit first light L2 of the SWIR band. Here, the second quantum dots QD2 emit the first light L2 emitted from the first quantum dot QD1, and when the second body portion 201B on which the second quantum dots QD2 are located is farther away from the detection unit 300 than the first body portion 201A, the sensing of the first light L2 by the detection unit 300 is not affected.

Unlike the above, when the second body portion 201B is closer to the detection unit 300 than the first body portion 201A due to the rotation of the micro robot 200', the second quantum dots QD2 absorb the first light L2 by itself, and thus the detection unit 300 may not sense the first light L2 or may sense second light L3 that has a lower intensity than that of the first light L2. Therefore, while the micro robot 200' rotates, the detection unit 300 may alternately sense the first light L2 and the second light L3 having different intensities from each other. The system for measuring behavior of the micro robot according to another embodiment may detect the rotating behavior of the micro robot by using a variation in the light intensity detected by the detection unit 300.

FIGS. 6 to 9 are diagrams illustrating a method of manufacturing the micro robot 200' according to another embodiment.

Figure 6:
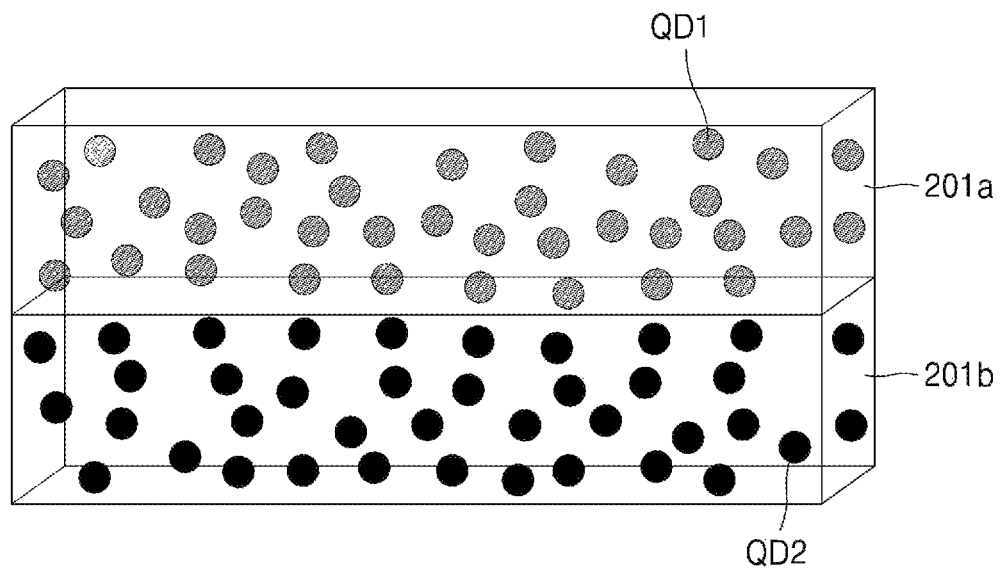
FIG. 6 is a diagram illustrating a method of manufacturing a micro robot according to another embodiment.

Referring to FIG. 6, according to the method of manufacturing the micro robot 200', a first photoresist substrate 201a including the first quantum dots QD1 and a second photoresist substrate 201b including the second quantum dots QD2 are prepared. Here, although not shown in the drawings, the above photoresist substrates may be provided, after preparing a base substrate, by forming the second photoresist substrate 201b on the base substrate and the first photoresist substrate 201a on the second photoresist substrate 201b, or vice versa. The first photoresist substrate 201a and the second photoresist substrate 201b may have the same materials as each other, except that the first and second photoresist substrates 201a and 201b respectively include the first quantum dots QD1 and the second quantum dots QD2, but one or more embodiments are not limited thereto.

Figure 7:
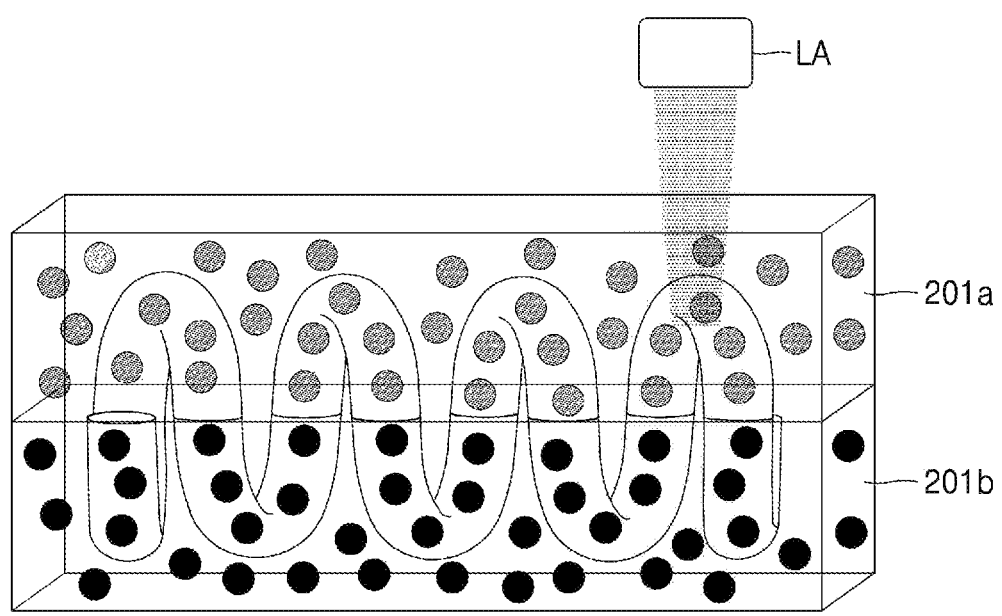
FIG. 7 is a diagram illustrating a method of manufacturing a micro robot according to another embodiment.
Figure 8:
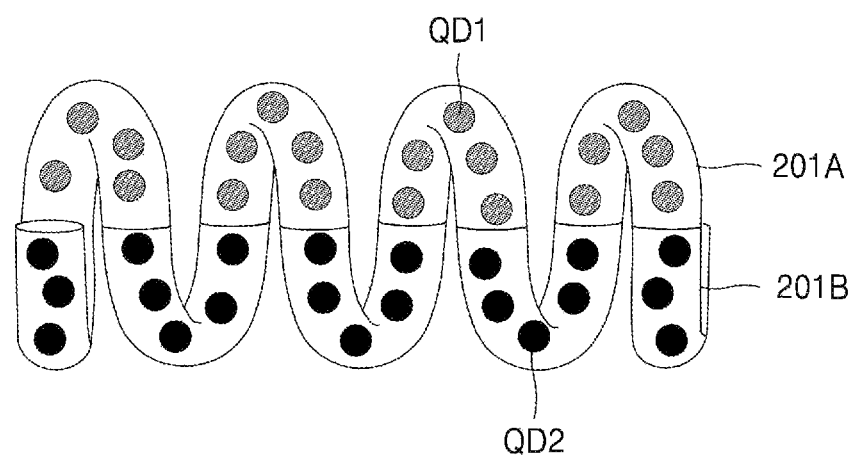
FIG. 8 is a diagram illustrating a method of manufacturing a micro robot according to another embodiment.

Referring to FIGS. 7 and 8, laser LA is irradiated onto the first photoresist substrate 201a and the second photoresist substrate 201b including a photo-curing material, in order to manufacture the first body portion 201A and the second body portion 201B each having a certain shape, in particular, a spiral shape or a pinwheel shape. Here, the photoresist material in the first body portion 201A is cured while the first quantum dots QD1 are included therein, and the photoresist material in the second body portion 201B is cured while the second quantum dots QD2 are included therein, to obtain the above structure. After that, a development process is performed, the photoresist PR that is not cured is removed from the first photoresist substrate 201a and the second photoresist substrate 201b, and then, the micro robot 200 as shown in FIG. 8 may be separated.

Figure 9:
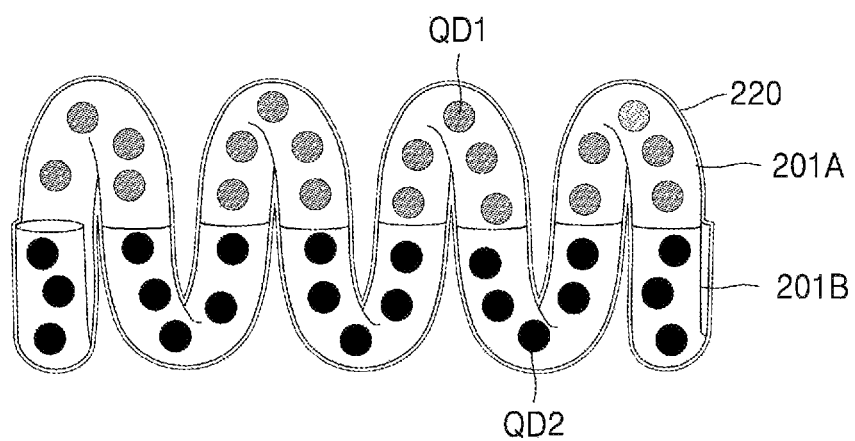
FIG. 9 is a diagram illustrating a method of manufacturing a micro robot according to another embodiment.

Referring to FIG. 9, the surface of the micro robot 200 separated through the above processes is coated with a thin film including a magnetic component and a biocompatible material, and then, the micro robot 200 that may be driven by an external magnetic field system may be finished.

The above method is an example of various methods of manufacturing the micro robot 200 according to the embodiment, and various manufacturing methods, in which the quantum dot is coated on the surface of the micro robot without forming the quantum dots in the micro robot, or an indicator including separate quantum dots is manufactured and coupled to the micro robot, may be used.

As described above, the measurement system for the behavior of the micro robot according to the embodiment may measure the behavior of the micro robot in real-time safely without hardware interference with the system driving the micro robot or a risk of radiation exposure, by irradiating light of the near infrared or SWIR wavelength band to the micro robot 200 including the quantum dots and sensing the light emitted from the micro robot. In particular, the measurement system for the behavior of the micro robot according to the embodiment may measure the rotating behavior of the micro robot by arranging the quantum dots of different kinds at different locations from each other.

As described above, the measurement system for the behavior of the micro robot according to the embodiment may measure the behavior of the micro robot in real-time safely without hardware interference with the system driving the micro robot or a risk of radiation exposure, by irradiating light of the near infrared or SWIR wavelength band to the micro robot including the quantum dots and sensing the light emitted from the micro robot. In particular, the measurement system for the behavior of the micro robot according to the embodiment may measure the rotating behavior of the micro robot by arranging the quantum dots of different kinds at different locations from each other.

However, the scope of the disclosure is not limited to the above effects.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A micro robot that is moveable in a body, the micro robot comprising:
    a body portion;
    first quantum dots arranged on a first area of the body portion; and
    second quantum dots arranged on a second area different from the first area of the body portion, the second quantum dots absorbing light emitted from the first quantum dots, wherein the first area and the second area are symmetrically arranged based on a first axis that is in parallel with a moving direction of the micro robot.

2. The micro robot of claim 1,
wherein the body portion comprising a magnetic portion, the body portion being moved by an external electromagnetic field.

3. The micro robot of claim 1, wherein the body portion is coated with the first quantum dots.

4. The micro robot of claim 2, wherein the first quantum dots absorb irradiated light of a near infrared ray wavelength band or a shortwave infrared ray (SWIR) band, and emit light of the SWIR band.

5. The micro robot of claim 1, further comprising:
an indicator located at an end or an intermediate portion of the body portion, the indicator having the first quantum dots arranged thereon.

6. The micro robot of claim 1,
wherein the first quantum dots are arranged inside the body portion.

7. The micro robot of claim 6, wherein the body portion is embedded with the first quantum dots.

8. A system for measuring a behavior of a micro robot, the system comprising:
a light source for irradiating light;
the micro robot comprising first quantum dots that absorb the light irradiated from the light source and emit light; and
a detection unit configured to sense the light emitted from the first quantum dots,
wherein the micro robot further comprising:
a body portion including a first area, the first quantum dots arranged on the first area; and
second quantum dots arranged on a second area different from the first area of the body portion, the second quantum dots absorbing light emitted from the first quantum dots,
wherein the first area and the second area are symmetrically arranged based on a first axis that is in parallel with a moving direction of the micro robot.

9. The system of claim 8, wherein:
the light source irradiates light of a near infrared ray wavelength band or a shortwave infrared ray (SWIR) wavelength band; and
the first quantum dots absorb the irradiated light of the near infrared ray wavelength band or the SWIR wavelength band and emit light of the SWIR wavelength band.

10. The system of claim 8, wherein the body portion comprising a magnetic portion.

11. The system of claim 8,
wherein
the detection unit detects rotation of the micro robot by using a difference in intensity of the detected light.

* * * * *